United States Patent
Tyrrell et al.

(10) Patent No.: US 9,931,679 B2
(45) Date of Patent: Apr. 3, 2018

(54) METHOD FOR CLEANING HARD SURFACES

(71) Applicant: KIMBERLY-CLARK WORLDWIDE, INC., Neenah, WI (US)

(72) Inventors: David J. Tyrrell, Milwaukee, WI (US); John Gavin MacDonald, Decatur, GA (US); Dave Allen Soerens, Neenah, WI (US); Paige Nicole Anunson, Larsen, WI (US); Douglas R. Hoffman, Oshkosh, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 15/108,589

(22) PCT Filed: Dec. 31, 2014

(86) PCT No.: PCT/US2014/072971
§ 371 (c)(1),
(2) Date: Jun. 28, 2016

(87) PCT Pub. No.: WO2015/103380
PCT Pub. Date: Jul. 9, 2015

(65) Prior Publication Data
US 2016/0325318 A1    Nov. 10, 2016

Related U.S. Application Data

(60) Provisional application No. 61/922,514, filed on Dec. 31, 2013.

(51) Int. Cl.
*B08B 7/00* (2006.01)
*A01N 25/10* (2006.01)
(Continued)

(52) U.S. Cl.
CPC ............ *B08B 7/0014* (2013.01); *A01N 25/10* (2013.01); *A01N 33/12* (2013.01); *A01N 59/00* (2013.01);
(Continued)

(58) Field of Classification Search
CPC ...... B08B 7/0014; A01N 25/10; A01N 33/12; A01N 59/00; A61L 2/18; A61L 2/186; A61L 2/22; A61L 2/235; A61L 2202/22
See application file for complete search history.

(56) References Cited

U.S. PATENT DOCUMENTS 3,179,955 A    4/1965  Worth
3,987,000 A   10/1976  Gleichenhagen et al.
(Continued)

FOREIGN PATENT DOCUMENTS

DE    10 2005 041 117 A1    3/2007
DE    102005041117 A1 *    3/2007
(Continued)

*Primary Examiner* — Sharidan Carrillo
(74) *Attorney, Agent, or Firm* — Kimberly-Clark Worldwide, Inc.

(57) ABSTRACT

An antibacterial cleaning composition for hard surfaces is made from a flexible superabsorbent material and an antibacterial agent. The composition can be applied to various liquid and solid surface contaminants, including blood, vomit, fecal matter, urine, glass, food, etc. The composition may be applied to the contaminated hard surface by several methods including pouring, rolling, spraying or foaming. Once cured, the antimicrobial cleaning composition is removed from the surface, taking the contaminant along with it and leaving behind a clean surface.

18 Claims, 7 Drawing Sheets

(51) Int. Cl.
  *A01N 33/12* (2006.01)
  *A61L 2/18* (2006.01)
  *A61L 2/22* (2006.01)
  *A61L 2/235* (2006.01)
  *A01N 59/00* (2006.01)

(52) U.S. Cl.
  CPC ............... *A61L 2/18* (2013.01); *A61L 2/186* (2013.01); *A61L 2/22* (2013.01); *A61L 2/235* (2013.01); *A61L 2202/22* (2013.01)

(56) References Cited

U.S. PATENT DOCUMENTS

| | | | |
|---|---|---|---|
| 5,196,185 | A | 3/1993 | Silver et al. |
| 5,205,864 | A | 4/1993 | Snyder |
| 5,359,735 | A | 11/1994 | Stockwell |
| 6,987,210 | B1 | 1/2006 | Giloh |
| 7,767,133 | B2 | 8/2010 | Giloh et al. |
| 8,088,315 | B2 | 1/2012 | Torres et al. |
| 8,096,979 | B2 | 1/2012 | Lina et al. |
| 8,124,549 | B2 | 2/2012 | Torres et al. |
| 8,450,389 | B1 | 5/2013 | Barefoot |
| 2004/0007534 | A1 | 1/2004 | Roach et al. |
| 2006/0138051 | A1 | 6/2006 | McGarvey et al. |
| 2008/0050410 | A1* | 2/2008 | Rogers ............... A01N 25/10 424/405 |
| 2008/0095812 | A1 | 4/2008 | Code |
| 2011/0172507 | A1* | 7/2011 | Lademann ......... A61F 13/0203 600/307 |
| 2013/0037048 | A1 | 2/2013 | Edgington et al. |
| 2013/0171024 | A1 | 7/2013 | Cuer et al. |
| 2015/0181863 | A1* | 7/2015 | Tyrrell ............... A01N 33/12 424/616 |
| 2016/0325318 | A1* | 11/2016 | Tyrrell ............... A01N 33/12 |

FOREIGN PATENT DOCUMENTS

| | | |
|---|---|---|
| JP | 2000-116264 A | 4/2000 |
| WO | WO 2000/076533 A1 | 12/2000 |
| WO | WO 2010/110898 A1 | 9/2010 |
| WO | WO2012001046 * | 1/2012 |

* cited by examiner

METHOD FOR CLEANING HARD SURFACES

CROSS-REFERENCE TO RELATED APPLICATIONS

This application claims the benefit of U.S. Provisional Application No. 61/922,514, filed Dec. 31, 2013, the subject matter therein incorporated by reference.

FIELD OF THE DISCLOSURE

The present disclosure relates generally to the field of the cleaning of hard surfaces, and more specifically to a method for cleaning contaminants, liquid or solid, from hard surfaces and disinfecting same.

BACKGROUND OF THE DISCLOSURE

Hospitals require that all hard surfaces in patient and treatment rooms be cleaned and disinfected. Targeted soils include, but are not limited to, biological soils that contain protein, such as blood. A two-step process is used to clean such soils from hard surfaces, one step for cleaning and another for disinfecting.

Cleaning the biological soils/blood routinely involves disposable wet wipes and/or non-disposable cloths that must be sanitized by laundering. Biological soils can be anywhere in the room, making cleanup with a wet wipe or cloth rather challenging (e.g. walls, equipment, connecting cables, etc.). After cleaning the biological soils from all hard surfaces, the same surfaces must be disinfected to eliminate infectious microorganisms left behind by biological soils. With an increase in multi-drug resistant organisms such as MRSA, there is a mandated time in which the disinfectant must make contact with infectious microorganisms.

Commonly, two staff members are needed to both clean and disinfect the room. This scenario is time consuming and costly.

There is a need for a less cumbersome and cost-effective method for cleaning and disinfecting biological soils or other contaminants from hard surfaces.

SUMMARY OF THE DISCLOSURE

In one aspect of the disclosure there is a method of disinfecting a hard surface which includes the following steps. First, provide an antimicrobial cleaning composition having a liquid flexible superabsorbent polymer material and an antibacterial agent having a disinfection period. Second, apply the antimicrobial cleaning composition onto the hard surface to be disinfected. Third, remove the dried antimicrobial cleaning composition from the hard surface. It may be desirable to allow the antimicrobial cleaning composition to cure no faster than the disinfection period.

In another aspect of the disclosure, there is a method of removing a contaminant from a hard surface and disinfecting same. First, provide an antimicrobial cleaning composition that includes an antimicrobial agent, a liquid superabsorbent polymer including acrylic acid, and an active agent. The antimicrobial agent is selected from a quaternary ammonium compound, a peroxide, a surfactant, silver, or copper, and combinations thereof. The active agent is selected from calcium chloride, glycerol, a surfactant, and combinations thereof. Second, apply the antimicrobial cleaning composition onto the hard surface so that it covers the contaminant. Third, dry the antimicrobial cleaning composition to induce cross-linking in the superabsorbent polymer material to transition the liquid composition into a solid state, and allow the antimicrobial cleaning composition to bond to the contaminant. Finally, remove the dried antimicrobial cleaning composition and bonded contaminant from the hard surface after the antimicrobial agent has effectively disinfected same.

In yet another aspect of the disclosure, there is a method of cleaning a contaminant from a hard surface. First, cover the contaminants with a liquid superabsorbent polymer comprising acrylic acid. Second, dry the liquid superabsorbent polymer so that it bonds to the contaminants. Third, remove the liquid superabsorbent polymer and contaminants from the hard surface.

The disclosure will be described in greater detail below by reference to particular embodiments illustrated in the drawings.

Definitions

It should be noted that, when employed in the present disclosure, the terms "comprises," "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

The term "binder" includes materials that are capable of attaching themselves to a substrate or are capable of attaching other substances to a substrate.

The term "polymers" includes, but is not limited to, homopolymers, copolymers, such as for example, block, graft, random and alternating copolymers, terpolymers, etc. and blends and modifications thereof. Furthermore, unless otherwise specifically limited, the term "polymer" shall include all possible configurational isomers of the material. These configurations include, but are not limited to isotactic, syndiotactic and atactic symmetries.

The term "solution" when used in the phrase "flexible superabsorbent binder polymer solution," and derivatives thereof, refers to a polymer solution that has not yet been substantially crosslinked (i.e., a precursor), but will result in the flexible superabsorbent binder polymer composition once crosslinking occurs.

The term "spontaneous crosslinking" refers to crosslinking, which occurs without radiation, catalysis, or any other inducement other than the specified temperature of not more than about 150° C., such as not more than about 120° C., or not more than about 100° C.

DETAILED DESCRIPTION

Reference will now be made in detail to embodiments of the disclosure, one or more examples of which are illustrated in the figures. Each example is provided by way of explanation of the disclosure, and not meant as a limitation of the disclosure. For example, features illustrated or described as part of one embodiment, may be used with another embodiment, to yield still a further embodiment. It is intended that the present disclosure include modifications and variations to the embodiments described herein.

The present disclosure is directed to a cleaning method for removing solid and liquid matter from a hard surface and disinfecting same. Various embodiments of the method of the present disclosure are pictured in FIGS. 1A-5B.

The antimicrobial cleaning composition used in the present disclosure generally includes an antimicrobial agent in a flexible binder superabsorbent polymer material. As used herein, the term "superabsorbent" refers to a water-swellable, water-insoluble organic or inorganic material capable, under the most favorable conditions, of absorbing at least about 10 times its weight or at least about 15 times its weight in an aqueous solution containing 0.9 weight percent sodium chloride. The superabsorbent material can be natural, synthetic, and modified natural polymers and materials. In addition, the superabsorbent materials can be inorganic materials, such as silica gels, or organic compounds such as cross-linked polymers.

Superabsorbent Material

A superabsorbent polymer material suitable for use in the present disclosure is described as a superabsorbent binder polymer solution in U.S. Pat. No. 6,849,685 to Soerens et al.; U.S. Pat. No. 7,312,286 to Lang et al.; U.S. Pat. No. 7,335,713 to Lang et al.; and U.S. Pat. No. 7,399,813 to Lang et al.: the entirety of each of these references is herein incorporated by reference. Such superabsorbent binder polymer solution may be referred to as flexible absorbent binder or "FAB" herein. The superabsorbent binder polymer solution described therein is capable of post-application, moisture-induced crosslinking. Whereas most superabsorbent polymers require the addition of an internal crosslinker to reinforce the polymer, the superabsorbent polymer material used in the present disclosure does not require the addition of a crosslinking agent because the organic monomers act as an internal crosslinker. The internal crosslinker allows the superabsorbent polymer material to be formed by coating the water-soluble precursor polymer onto the substrate and then removing the water to activate the latent crosslinker.

Lang et al., in U.S. Pat. No. 7,335,713, the entirety of which is herein incorporated by reference, describes an absorbent binder composition that may be used as a superabsorbent polymer material in the present disclosure. The absorbent binder composition disclosed in Soerens et al. is a monoethylenically unsaturated polymer and an acrylate or methacrylate ester that contains an alkoxysilane functionality that is particularly suitable for use in manufacturing absorbent articles. Also described in Lang et al. is a method of making the absorbent binder composition that includes the steps of preparing a monomer solution, adding the monomer solution to an initiator system, and activating a polymerization initiator within the initiator system reported an aqueous-based, water-soluble binder composition. "Monomer(s)" as used herein includes monomers, oligomers, polymers, mixtures of monomers, oligomers and/or polymers, and any other reactive chemical species which are capable of co-polymerization with monoethylenically unsaturated carboxylic, sulphonic or phosphoric acid or salts thereof. Ethylenically unsaturated monomers containing a trialkoxysilane functional group are appropriate for this disclosure and are desired. Desired ethylenically unsaturated monomers include acrylates and methacrylates, such as acrylate or methacrylate esters that contain an alkoxysilane functionality.

The absorbent binder composition disclosed in the references noted above is the reaction product of at least 15 percent by mass monoethylenically unsaturated carboxylic, sulphonic or phosphoric acid or salts thereof, an acrylate or methacrylate ester that contains an alkoxysilane functionality which, upon exposure to water, forms a silanol functional group which condenses to form a crosslinked polymer, a copolymerizable hydrophilic glycol containing ester monomer; and/or, a plasticizer.

Desirably, the monoethylenically unsaturated monomer is acrylic acid. Other suitable monomers include carboxyl group-containing monomers: for example monoethylenically unsaturated mono or poly-carboxylic acids, such as (meth)acrylic acid (meaning acrylic acid or methacrylic acid; similar notations are used hereinafter), maleic acid, fumaric acid, crotonic acid, sorbic acid, itaconic acid, and cinnamic acid; carboxylic acid anhydride group-containing monomers: for example monoethylenically unsaturated polycarboxylic acid anhydrides (such as maleic anhydride); carboxylic acid salt-containing monomers: for example water-soluble salts (alkali metal salts, ammonium salts, amine salts, and the like) of monoethylenically unsaturated mono- or poly-carboxylic acids (such as sodium (meth) acrylate, trimethylamine (meth)acrylate, triethanolamine (meth)acrylate), sodium maleate, methylamine maleate; sulfonic acid group-containing monomers: for example aliphatic or aromatic vinyl sulfonic acids (such as vinylsulfonic acid, allyl sulfonic acid, vinyltoluenesulfonic acid, styrene sulfonic acid), (meth)acrylic sulfonic acids [such as sulfopropyl (meth)acrylate, 2-hydroxy-3-(meth)acryloxy propyl sulfonic acid]; sulfonic acid salt group-containing monomers: for example alkali metal salts, ammonium salts, amine salts of sulfonic acid group containing monomers as mentioned above; and/or amide group-containing monomers: vinylformamide, (meth)acrylamide, N-alkyl (meth)acrylamides (such as N-methylacrylamide, N-hexylacrylamide), N,N-dialkyl (meth)acryl amides (such as N,N-dimethylacrylamide, N,N-di-n-propylacrylamide), N-hydroxyalkyl (meth)acrylamides [such as N-methylol (meth)acrylamide, N-hydroxyethyl (meth)acrylamide], N,N-dihydroxyalkyl (meth)acrylamides [such as N,N-dihydroxyethyl (meth) acrylamide], vinyl lactams (such as N-vinylpyrrolidone).

Suitably, the amount of monoethylenically unsaturated carboxylic, sulphonic or phosphoric acid or salts thereof relative to the weight of the absorbent binder polymer composition may range from about 15 percent to about 99.9 percent by weight. The acid groups are desirably neutralized to the extent of at least about 25 mol percent, that is, the acid groups are preferably present as sodium, potassium or ammonium salts. The degree of neutralization is desirably at least about 50 mol percent.

Organic monomers capable of co-polymerization with monoethylenically unsaturated carboxylic, sulphonic or phosphoric acid or salts thereof, which monomers contain a trialkoxysilane functional group or a moiety that reacts with water to form a silanol group, are useful in the practice of this invention. The trialkoxysilane functional group has the following structure:

wherein $R_1$, $R_2$ and $R_3$ are alkyl groups independently having from 1 to 6 carbon atoms.

Whereas most superabsorbent polymers require addition of an internal crosslinker to reinforce the polymer, the flexible superabsorbent binder polymer composition of the present invention does not require the addition of a cross-linking agent because the organic monomers including the trialkoxysilane function as an internal crosslinker. The internal crosslinker allows the superabsorbent binder polymer composition to be formed by coating the water-soluble precursor polymer onto the substrate and then removing the water to activate the latent crosslinker.

In addition to monomers capable of co-polymerization that contain a trialkoxysilane functional group, it is also feasible to use a monomer capable of co-polymerization that can subsequently be reacted with a compound containing a trialkoxysilane functional group or a moiety that reacts with water to form a silanol group can also be used. Such a monomer may contain, but is not limited to, an amine or an alcohol. An amine group incorporated into the co-polymer may subsequently be reacted with, for example, but not limited to, (3-chloropropyl)trimethoxysilane. An alcohol group incorporated into the co-polymer may subsequently be reacted with, for example, but not limited to tetramethoxysilane.

The amount of organic monomer having trialkoxysilane functional groups or silanol-forming functional groups relative to the weight of the polymeric binder composition may range from about 0.1% to about 15% by weight. Suitably, the amount of monomer should exceed 0.1% by weight in order provide sufficient crosslinking upon exposure to moisture. In some aspects, the monomer addition levels are between about 0.1% and about 20% by weight of the flexible superabsorbent binder polymer composition, such as, between about 0.5% and about 10% by weight of the flexible superabsorbent binder polymer composition; or between about 0.5% and about 5% by weight of the flexible superabsorbent binder polymer composition for some intended uses. The flexible superabsorbent binder polymer composition can include a copolymerizable hydrophilic glycol containing an ester monomer, for example a long chain, hydrophilic monoethylenically unsaturated esters, such as poly(ethylene glycol) methacrylate having from 1 to 13 ethylene glycol units. The hydrophilic monoethylenically unsaturated esters have the following structure:

R=H or $CH_3$
R'=H, alkyl, phenyl

The amount of monoethylenically unsaturated hydrophilic esters relative to the weight of the polymeric binder composition thereof may range from 0 to about 75% by weight of monomer to the weight of the flexible superabsorbent binder polymer composition. In some aspects, the monomer addition levels are between about 10% and about 60% by weight of the flexible superabsorbent binder polymer composition; such as between about 20% and about 50% by weight of the flexible superabsorbent binder polymer composition; or between about 30% and about 40% by weight of the flexible superabsorbent binder polymer composition for some intended uses.

In some aspects, the flexible superabsorbent binder polymer composition may also include a hydrophilic plasticizer. Suitable hydrophilic plasticizers that may be used include, but are not limited to a polyhydroxy organic compounds such as glycerin, and low molecular weight polyolefinic glycols such as polyethylene glycol (PEG) of molecular weight ranges from about 200 to about 10,000.

The amount of plasticizer relative to the weight of the flexible superabsorbent binder polymer composition thereof may range from 0 to about 75% by weight of plasticizer to the weight of the flexible superabsorbent binder polymer composition. In some aspects, the plasticizer addition levels are from about 10% to about 60% by weight of the flexible superabsorbent binder polymer composition; such as from about 10% to about 40% by weight of the flexible superabsorbent binder polymer composition for some intended uses.

In some aspects, the flexible superabsorbent binder polymer composition of the present invention may be made from monomers that include at least 15% by weight monoethylenically unsaturated monomer selected from carboxylic acid, carboxylic acid salts, sulphonic acid, sulphonic acid salts, phosphoric acid, or phosphoric acid salts; an initiator system; and an acrylate or methacrylate ester that contains a group readily transformed into a silanol functionality by subsequent reaction with water, wherein said the resulting flexible superabsorbent binder polymer composition has an average molecular weight of from about 100,000 to about 650,000 g/mole, such as about 100,000 to about 300,000 g/mole, and the superabsorbent polymer composition has a viscosity of less than about 10,000 cps and a residual monoethylenically unsaturated monomer content of less than about 1000 ppm.

One of the issues in preparing water-soluble polymers is the amount of the residual monoethylenically unsaturated monomer content remaining in the polymer. For applications in personal hygiene it is required the amount of residual monoethylenically unsaturated monomer content of the superabsorbent polymer composition be less than about 1000 ppm, and more preferably less than 500 ppm, and even more preferably less than 100 ppm. U.S. Pat. Nos. 7,312,286; 7,335,713 and 7,339,813 disclose at least one method by which an absorbent binder composition may be manufactured so that the residual monoethylenically unsaturated monomer content is at least less than 1000 parts per million. The analysis of residual monoethylenically unsaturated monomer is determined according to the Residual Monoethylenically Unsaturated Monomer Test which is disclosed in U.S. Pat. No. 7,312,286. More specifically, the residual monoethylenically unsaturated monomer analysis is carried out using solid film obtained from the polymer solution or superabsorbent composition. By way of example for this test description, the monoethylenically unsaturated monomer is acrylic acid. High performance liquid chromatography (HPLC) with a SPD-IOAvp Shimadzu UV detector (available from Shimadzu Scientific Instruments, having a place of business in Columbia, Md., U.S.A) is used to determine the residual acrylic acid monomer content. To determine the residual acrylic acid monomer, about 0.5 grams of cured film is stirred in 100 ml of a 0.9% NaCl-solution for 16 h using a 3.5 cm L×0.5 cm W magnetic stirrer bar at 500 rpm speed. The mixture is filtered and the filtrate is then passed through a Nucleosil C8 100A reverse phase column (available from Column Engineering Incorporated, a business having offices located in Ontario, Calif., U.S.A.) to separate the acrylic acid monomer. The acrylic acid monomer elutes at a certain time with detection limit at about 10 ppm. The peak area of resulting elutes calculated from the chromatogram is then used to calculate the amount of residual acrylic acid monomer in the film. Initially, a calibration curve was generated by plotting the response area of pure acrylic acid elutes against its known amount (ppm). A linear curve with a correlation coefficient of greater than 0.996 was obtained.

A method for disinfecting a hard surface includes the step of providing an antimicrobial cleaning composition which may have a viscosity that permits delivery of the antimicrobial cleaning composition through a conventional spray bottle (e.g. a hand operated spray bottle). In such embodiments, the viscosity of the superabsorbent polymer material within the antimicrobial cleaning composition is less than about 10,000 cP and greater than about 500 cP. In other embodiments, the viscosity of the superabsorbent polymer material is preferably less than 2,000 cP and more preferably less than 1000 cP. In some embodiments, the viscosity of the superabsorbent polymer material is greater than 500 cP, and in other embodiments greater than 650 cP. A higher viscosity may be desired for application by pouring or rolling, e.g. 50,000 cP or more. (The viscosity of the superabsorbent polymer material is measured at 16 hours according to the test procedure outlined in U.S. Pat. No. 7,312,286. As explained therein, the viscosity of the superabsorbent polymer material is measured using a Brookfield DVII+ Programmable viscometer which is available from Brookfield Engineering, Middleboro, Mass., U.S.A. About 200-250 ml of the superabsorbent polymer material is taken in a 25-ounce plastic cup. The viscometer is generally zeroed initially with a desired Spindle. For the superabsorbent polymer material, Spindle Number 3 is used. The viscosity is measured at 20 RPM and at temperature of 22.±0.1 degrees C.)

Desirably, the absorbent capacity of the superabsorbent polymer material or composition alone is at least one (1) gram of fluid per gram of superabsorbent polymer material, and in some embodiments at least three (3) grams of fluid per gram of superabsorbent polymer material, when measured using the Centrifuge Retention Capacity Test described in U.S. Pat. No. 7,312,286.

In selected embodiments, the retention capacity of the porous absorbent structure of the present disclosure is preferably greater than 10 g/g, and more preferably is greater than 12 g/g when measured using the Centrifuge Retention Capacity Test described herein.

Antimicrobial Agents

Suitable antimicrobial agents include quaternary ammonium compounds (didecyl dimethyl ammonium chloride, benzethonium chloride, cetrimonium chloride, cetylpyridinium chloride, cocamidopropyl PG-dimonium chloride phosphate, cetrimide, didecyl dimethyl ammonium carbonate, didecyl dimethyl ammonium bicarbonate), peroxides (hydrogen peroxide, urea hydrogen peroxide, benzoyl peroxide, calcium peroxide, magnesium peroxide, zinc peroxide, polyvinylpyrollidone-hydrogen peroxide), surfactants, silver and/or copper particles or ions, biguanides (chlorhexidine digluconate, chlorhexidine diacetate, chlorhexidine dihydrochloride, polyhexamethylene biguanide), isothiazolinones (methylisothiazolinone, methylchloroisothiazolinone, benzisothiazolinone, octylisothiazolinone), alcohols (ethanol, isopropanol), acids (benzoic acid, boric acid, citric acid, lactic acid, malic acid, maleic acid), hypochlorites (sodium hypochlorite, calcium hypochlorite), iodine, phenolics (chloroxylenol, hexachlorophene, triclosan, salicyclic acid, thymol, o-phenylphenol, cresols), potassium monopersulfate, chlorine dioxide, anilides (triclocarban, tribromsalan), pyrithiones, and antimicrobial peptides. For instance quaternary ammonium compounds (otherwise referred to as "quats") include benzalkonium chloride (USP Mason Chemical, Arlington Heights, Ill.). In one embodiment, suitable peroxides include organic peroxides such as hydrogen peroxide (Sigma-Aldrich Chemical Co., Milwaukee, Wis.). In another embodiment, suitable silver materials include silver nitrate, silver oxide, and silver metal particles (e.g. SILVAGARD®, available from AcryMed Inc., Beaverton, Oreg., USA). In yet another embodiment, suitable copper materials include copper nitrate, copper chloride and copper sulfate.

Ingredients capable of manipulating the release kinetics of the actives may also be present, including but not limited to polymers and salts. Polymer and salt selection is dependent upon which active(s) is present in the composition.

Additionally, it may be desirable that the polymer have an exothermic reaction upon use to enhance the removal of organic material or enhance the activity of the antimicrobial agents. Ingredients that would drive an exothermic reaction in the composition during use may include but is not limited to anhydrous salts such as magnesium chloride or ferric chloride, desiccants such as magnesium and calcium sulfate, supersaturated salt solutions, and zeolites. Such an attribute would necessitate the use of packaging that keeps the exothermic ingredient separate from the water phase of the composition. The exothermic ingredient and the water phase would then come in contact at the point of use of the composition.

Additional Active Agents

After mixing the antimicrobial agent into the superabsorbent polymer material and attaining the desired weight ratio, other active agents may be added to the antimicrobial cleaning composition.

Polyol: A polyol such as glycerol may be added to the composition of superabsorbent polymer material and antimicrobial agent to increase the flexibility of the porous absorbent material. Other additives may be utilized to increase the flexibility and integrity of the superabsorbent material. For example, some embodiments may include poly(ethylene glycol) (PEG) having a molecular weight of 8000 in an amount of approximately fifteen percent (15%) by weight.

Foaming Agent: The purpose of the foaming agent is to cause foaming of the FAB immediately after application to a hard surface.

Calcium Chloride: The purpose of adding calcium chloride is to speed the curing time of the antimicrobial cleaning composition. An effective amount is added such that the curing time of the antimicrobial cleaning composition is at least as long as the time period required for the antimicrobial agent to disinfect the hard surface.

Dye: A dye may be added to the antimicrobial cleaning composition for aesthetic and functional reasons. Without a dye, the antimicrobial cleaning composition is somewhat colorless. By adding a dye, one will be able to observe whether or not the composition has adequately covered a desired area. In one aspect, the antimicrobial cleaning composition may come in an array of colors specific to whatever contaminant is being cleaned. For example, a color such as blue may be used because it is typically associated with a feeling of sanitation. In another non-limiting example, vomit may be cleaned with a green composition, blood with a red composition, general cleaning with a blue composition, glass pick-up with a purple composition, and so forth.

Fragrance: An odor masking or absorbing fragrance may be added to the antimicrobial cleaning composition. Suitable fragrances are water soluble.

Texturizing Particles

In one aspect of the disclosure, inorganic "texturizing" particles may be added to the superabsorbent polymer material to form a mixture which has not yet been substantially cross-linked, but will result in a porous, "textured" absorbent structure when cross-linking occurs. This is advantageous when there may be foot traffic over the dried composition of the present disclosure. Suitable inorganic particles include but are not limited to Arizona sand, pumice, diatomaceous earth and chalk. In selecting texturizing particles, care must be taken to avoid increasing the cross-linking of the superabsorbent polymer material to a level high enough that the resulting material becomes too brittle to maintain integrity and function properly as an absorbent material.

The size of the inorganic texturizing particles is preferably chosen to achieve a gritty feel to the cured antimicrobial cleaning composition without interfering with the delivery method of the composition. For example, certain particles may clog a typical spray bottle. Particles having an average ratio of length to width of less than about 5 are desirable. Even more desirable are texturizing particles having an average ratio of length to width of less than about 3. In many desired aspects of the disclosure, the texturizing particles have an average length of greater than about 20 microns and less than about 80 microns.

Texturizing particles may be added to the FAB so that the ratio by weight of superabsorbent polymer material to particles is greater than about 3:1, and in some embodiments is greater than or equal to 3.5:1. In selected embodiments the ratio by weight of superabsorbent polymer material to texturizing particles in the mixture is less than about 6:1. In certain embodiments, texturizing particles are added into the superabsorbent polymer material to form a mixture wherein the ratio by weight of superabsorbent polymer material to texturizing particles in the mixture is greater than 3:1 and less than about 6:1. Ratios within these ranges enable formation of porous absorbent structures with suitable integrity.

Method of Use

The antibacterial composition of the present disclosure is applied to a hard surface area containing a solid or liquid contaminant such as particulates (e.g. glass, dust, food stuff, and the like), body matter (e.g. oils, blood, vomit, saline, human tissue, gastric juices, fecal matter, mucus, urine, and the like), and any other contaminant imaginable in a setting requiring disinfection of hard surfaces (e.g. hospitals, clinics, schools, day cares, theaters, shopping centers, public transportation, etc.).

In one aspect of the disclosure is a method of cleaning or disinfecting a hard surface that includes the step of providing a mixture of liquid superabsorbent polymer material and antibacterial agent, which together are referred to as the "antimicrobial cleaning composition." In other embodiments, the method of claim 1 further includes the step of adding texturizing particles to the antimicrobial cleaning composition, as described above.

Each possible antibacterial agent has a "disinfection period" defined herein as the period of time in which the agent needs to contact the contaminant to achieve disinfection. For example, some antibacterial agents such as certain quaternary ammonium agents require a disinfection period of several minutes during which the antibacterial agent remains wet and in contact with the contaminant. Because of the need for the antibacterial agent to remain wet in order to kill microbes or eradicate other contaminants such as viruses, the superabsorbent polymer material should not completely dry into a solid before the disinfection period has expired.

The antimicrobial cleaning composition may be applied to the contaminated hard surface in a number of ways such as by pouring, or by spraying with a spray bottle or compressed air sprayer, or by rolling (e.g. rolling on with a paint roller). In one embodiment, the sprayed antimicrobial cleaning composition foams upon spraying. Regardless of the application method, the entire contaminated area should be covered by the antimicrobial cleaning composition (see, FIGS. 1A, 2A, 3A, 4A and 5A).

The antimicrobial cleaning composition is then allowed to dry ("cure") into a solid such as by cross-linking. Desirably, the curing time is no faster than the disinfection period, though there may be some applications were disinfection is not needed, such as when the antibacterial cleaning composition is used to clean up debris such as broken glass (see FIGS. 1A-B). The contaminant bonds to the antimicrobial cleaning composition at least physically.

Once cured, the antimicrobial cleaning composition is peeled away or otherwise removed from the hard surface, leaving a clean and disinfected surface. See for example. FIGS. 2B, 3B, 4D and 5B.

The cleaning method of the present disclosure has several advantages over traditional cleaning means. First, the method does not require separate pick-up and disinfection steps. Second, the method does not require tedious cleaning around raised surfaces such as a keyboard. This saves a significant amount of time and labor. Other advantages will be apparent in the present description.

EXAMPLES

The following examples are provided to illustrate the invention and do not limit the scope of the claims. Unless otherwise stated, all parts and percentages are by weight.

The following description in Example 1 and the specific proportional amounts of all ingredients for larger volume of flexible absorbent binder polymer solutions preparation as set forth in Table 2 provide the basis for Examples 1-4.

Examples 1-4

First, a pre-neutralized (about 60% degree of neutralization, DN) monomer solution was prepared by the following method. About 180 g water was added into a 1-L beaker equipped with a magnetic stirrer and a temperature probe. To the water, 59.23 g of glacial acrylic acid was added with stirring. Next, 39.5 g of 50% aq. NaOH was added slowly to the aqueous solution with a moderate speed of stirring. This aqueous solution was cooled to about 30° C. in a water bath, and another aliquot of 59.25 g glacial acrylic acid was added to the aqueous solution. A second aliquot of 39.5 g 50% aq.

NaOH was added slowly to the aqueous solution. The neutralized acrylic acid solution was cooled to about 25-30° C. in a water bath.

To the pre-neutralized monomer solution, 0.3 g of 50% w/w hypophosphorous acid solution (chain transfer agent) was added.

A homogenous mixture of 17.5 g polyethylene glycol (PEG) 400 and 2.1 mL of 3 (trimethoxysilyl)propyl methacrylate (MEMO) crosslinker was prepared by adding MEMO into PEG with rapid stirring. This mixture was then added to preneutralized monomer solution, and the mixture was well stirred for a few minutes.

Two initiator system solutions were prepared by dissolving 1.71 g sodium erythorbate (SEB) in 18.96 g water and by dissolving 4.56 g 35% H2O2 in 17.73 g water.

The polymerization was carried out as follows: Into a 1-L jacketed glass reactor, 195.6 g previously sparged water with N2 gas was added. The temperature of this heel water was kept at 22-24° C. The slow flowing N2 gas, the preneutralized monomer solution, and the two initiator system solutions were introduced into a reactor via three inlets in the reactor lid. Each of the two initiator system solutions were introduced into the reactor through the inlets of opposite sides of the reactor. The monomer and initiator solutions were added drop wise by three peristaltic pumps simultaneously for a predetermined period of time at predetermined dosage rates while the reaction solution water was being stirred under a slow stream of N2 gas. The peristaltic pumps were previously calibrated for desired flow rate of each solution. The polymerization reaction kinetics data was monitored and recorded by a data acquisition software for recording temperature change as a function of time. The preneutralized monomer solution was added over a period of time, usually between 30 minutes and 120 minutes, but typically 60 minutes. The two initiator system solutions were added both during the polymerization procedure and for an additional 60 minutes beyond the monomer addition time.

The solution temperature starts to increase after 6-8 minutes of addition of reactants and continues to gradually climb. The temperature of the reaction was allowed to reach a predetermined maximum temperature, usually between 40 and 70° C., and most typically 60° C. This temperature was maintained by circulating cooling water through the reactor.

During the preneutralized monomer addition, the initiator solutions are added at a rate such that half of the solutions described above are added during the monomer addition. After the monomer feed is completed, the rate of the initiator solutions addition was altered such that the remaining half of each solution was added during a 30-minute period. Then, additional SEB and H2O2 solutions at concentrations of SEB 1.31 g in 14.60 g water and 1.31 g 35% H2O2 in 5.05 g water were added for additional 30 minutes as a kill for residual monomer. The speeds of the peristaltic pumps used to dose the initiator solutions were adjusted such that appropriate feed rates were obtained.

After the completion of all initiator solutions additions, the polymerization solution was stirred for additional 90 minutes. At this time, the polymerization solution starts to cool down gradually. After 90 minutes of additional stirring, the polymer solution is cooled to approximately (~) 30° C. by circulating water through the jacket of the reactor. 22.35 g of 50% NaOH solution was added to post-neutralize the superabsorbent polymer binder solution to a final degree of neutralization of 77%. Cooling was continued during the addition of the sodium hydroxide post-neutralization such that the temperature of the reaction mixture does not exceed 45° C. The resulting polymer solution was stirred for approximately 5-30 minutes after the addition of NaOH. The polymer solution was then cooled to ~30° C. again by circulating water through the jacket of the reactor.

Table 1 includes information about the properties of the solution and the resulting flexible absorbent binder.

TABLE 1

| | | Solution Properties | | | | Performance Characteristics of Flexible Absorbent Binder | | | |
|---|---|---|---|---|---|---|---|---|---|
| Sample ID | Wt of FAB Solution (LB) | % Solids | Visc. (cPs) | Solution Residual Acrylic Acid (ppm) | Color | Product Residual Acrylic Acid (ppm) | GRC g/g | NRC g/g | Color |
| Ex. 1 | 1.28 | — | — | 415 | Clear, Colorless | BDL | 16.2 | 22.6 | None |
| Ex. 2 | 215 | | | 482 | Clear, Colorless | 964 | 14.0 | 20.5 | None |
| Ex. 3 | 1050 | 33.5 | 585 | 307 | Clear, Colorless | 254 | 12.3 | 18.9 | None |
| Ex. 4 | 1450 | 33.7 | 1280 | 2863 | Clear, Colorless | 698 | 14.7 | 21.1 | None |

The following examples demonstrate how the flexible binder superabsorbent material (FAB) and the antimicrobial cleaning composition collects solid matter and absorbs liquid matter.

Example 5

Figure 1A:
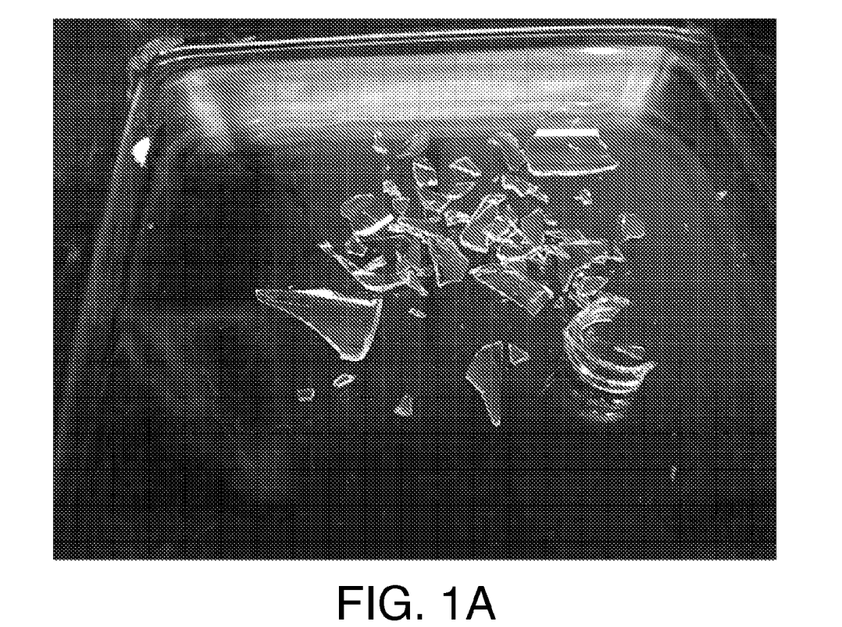
FIG. 1A is a photograph of a tray of broken glass.
Figure 1B:
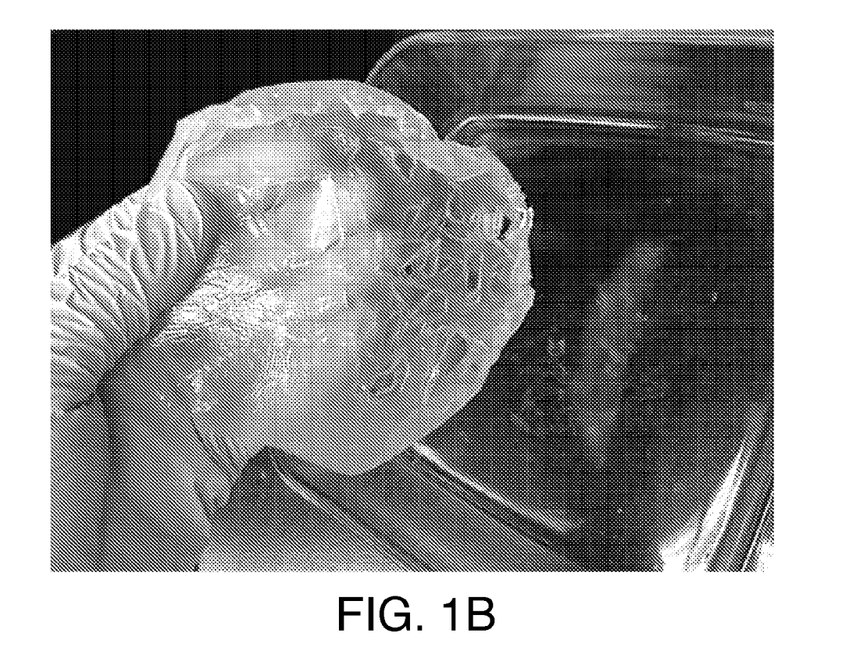
FIG. 1B is a photograph of the broken glass of FIG. 1A embedded into a polymeric material of the present disclosure.

Now, referring to FIG. 1A, shown is a photograph of a PYREX glass dish containing broken glass. 10 g of antimicrobial cleaning composition (FAB containing 5% wt/wt benzalkonium chloride and 3% wt/wt hydrogen peroxide) was applied to the area containing the glass debris. FIG. 1B is a photograph of the broken glass embedded into or at least covered by the polymeric composition of the present disclosure. The antimicrobial cleaning composition covers the glass pieces and shards, reducing sharpness so that they can be handled with less concern of being cut.

Example 6

Figure 2A:
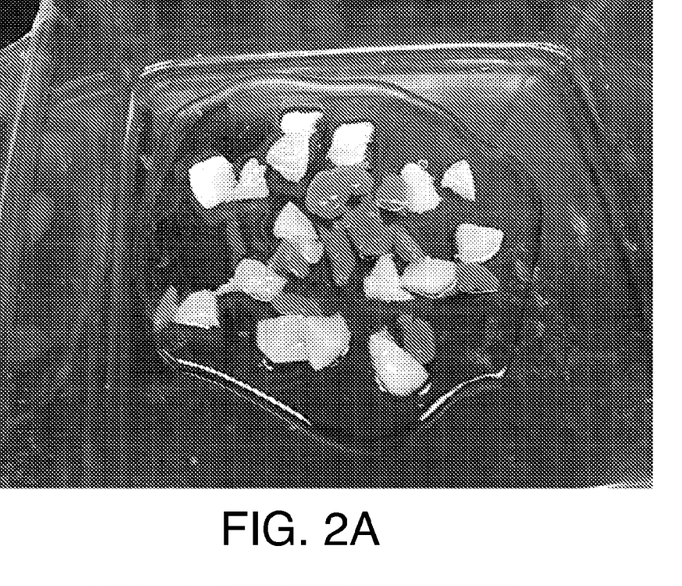
FIG. 2A is a photograph of fruit salad in juice spilled onto a PYREX glass dish.
Figure 2B:
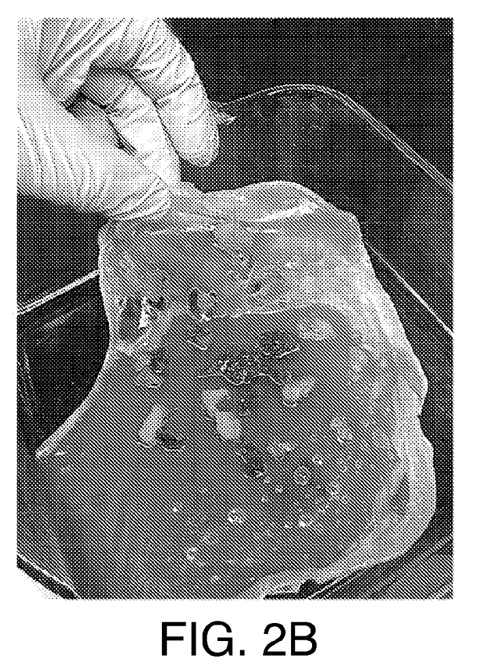
FIG. 2B is a photograph of the fruit salad and juice of FIG. 2A completely absorbed into the polymeric material of the present disclosure.

Referring now to FIG. 2A, shown is a photograph of 25 g of canned fruit salad packed in juice spilled onto a PYREX glass dish. 40 g of the antimicrobial cleaning composition (FAB containing 5% wt/wt benzalkonium chloride and 3% wt/wt hydrogen peroxide) was applied to the food. FIG. 2B is a photograph of the fruit salad and juice of FIG. 2A completely collected by and absorbed into the polymeric material of the present disclosure, even to the point where the fruit was partially desiccated by the antimicrobial cleaning composition. The cured polymeric composition was then peeled away leaving behind a clean and disinfected dish.

Example 7

Figure 3A:
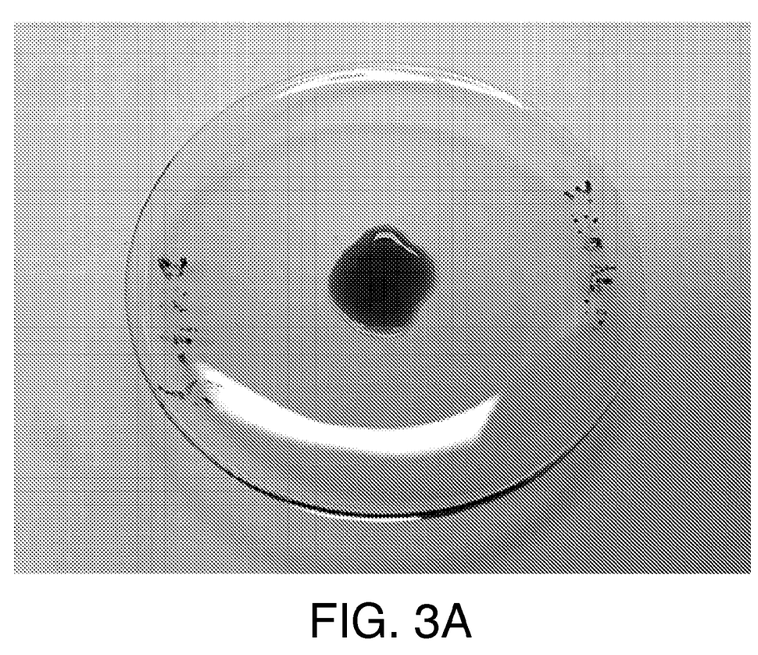
FIG. 3A is a photograph of a PYREX glass dish containing liquid blood.
Figure 3B:
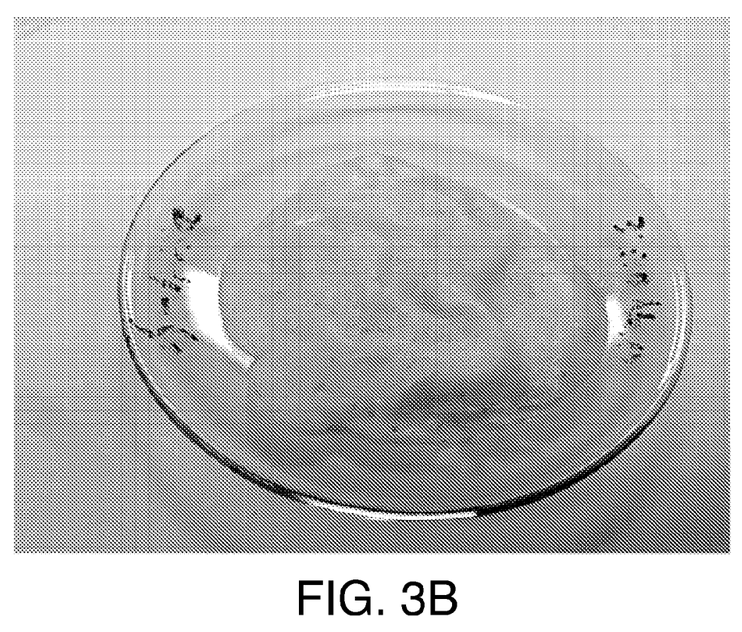
FIG. 3B is a photograph of the blood completely absorbed by the polymeric material of the present disclosure.

Referring now to FIG. 3A, shown is a photograph of a PYREX glass dish containing 1 g of liquid bovine blood from a calf liver (SKYLARK, American Foods Group, LLC, Omaha, Nebr.). 10 g of the antimicrobial cleaning composition (FAB containing 5% wt/wt benzalkonium chloride and 3% wt/wt hydrogen peroxide) was applied to the blood, completely covering same. FIG. 3B is a photograph of the blood completely absorbed by the antimicrobial cleaning composition of the present disclosure. One may note that the antimicrobial cleaning composition discolored the blood.

Example 8

Figure 4A:
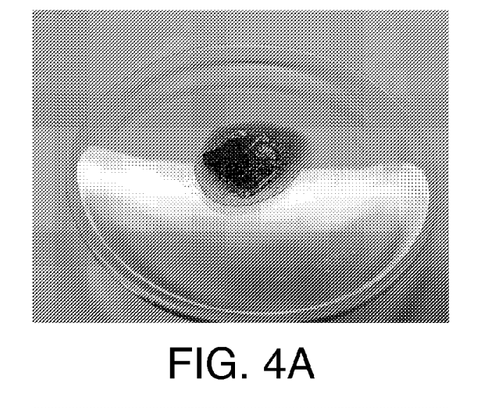
FIGS. 4A to 4D is a series of photographs demonstrating how the polymeric material of the present disclosure can absorb dried blood.
Figure 4B:
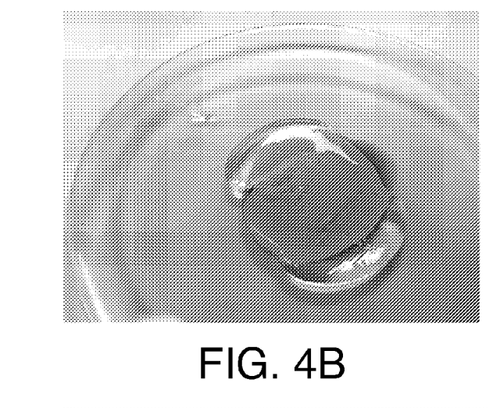
Figure 4C:
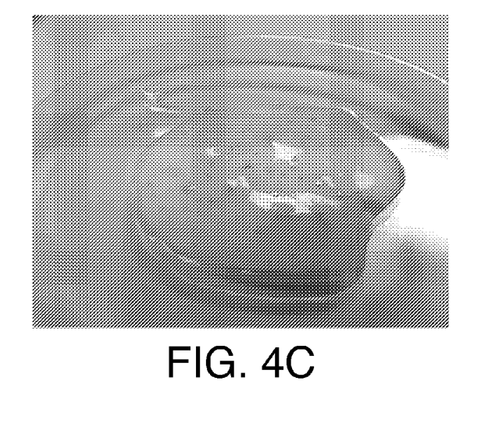
Figure 4D:
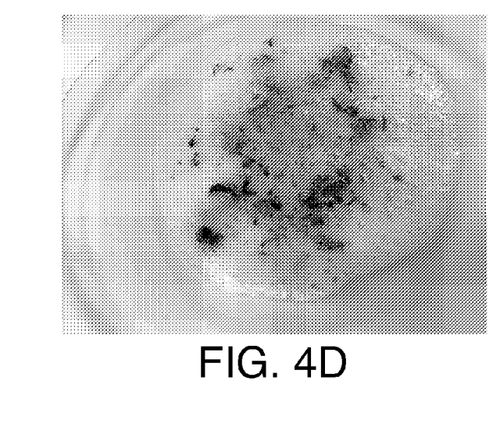

Referring now to FIGS. 4A to 4D, shown is a series of photographs demonstrating how the polymeric material of the present disclosure can absorb dried blood. FIG. 4A shows some bovine blood in a PYREX glass dish, dried in a lab under ambient conditions. An effective amount of the antimicrobial cleaning composition (FAB containing 5% wt/wt benzalkonium chloride and 3% wt/wt hydrogen peroxide) was poured over the dried blood, covering it completely, see FIG. 4B. The composition foamed as it reconstituted the blood, see FIG. 4C. (The foaming reaction was not due to the presence of an additive.) The cured composition contained dried blood fragments (see FIG. 4D) which were lifted away when the composition was removed from the dish.

Example 9

Figure 5A:
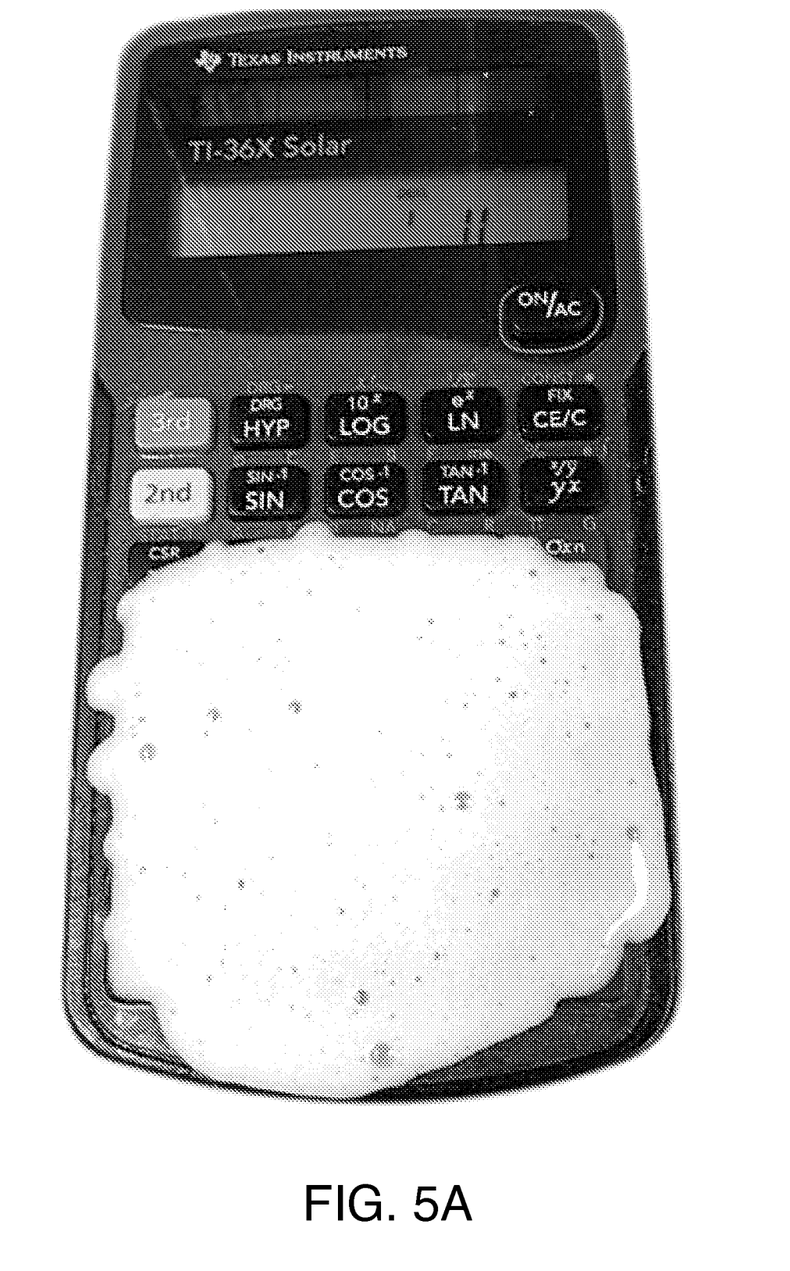
FIGS. 5A and 5B are photographs showing the polymeric material of the present disclosure as applied to a keyboard of a calculator, and the subsequent removal thereof.
Figure 5B:
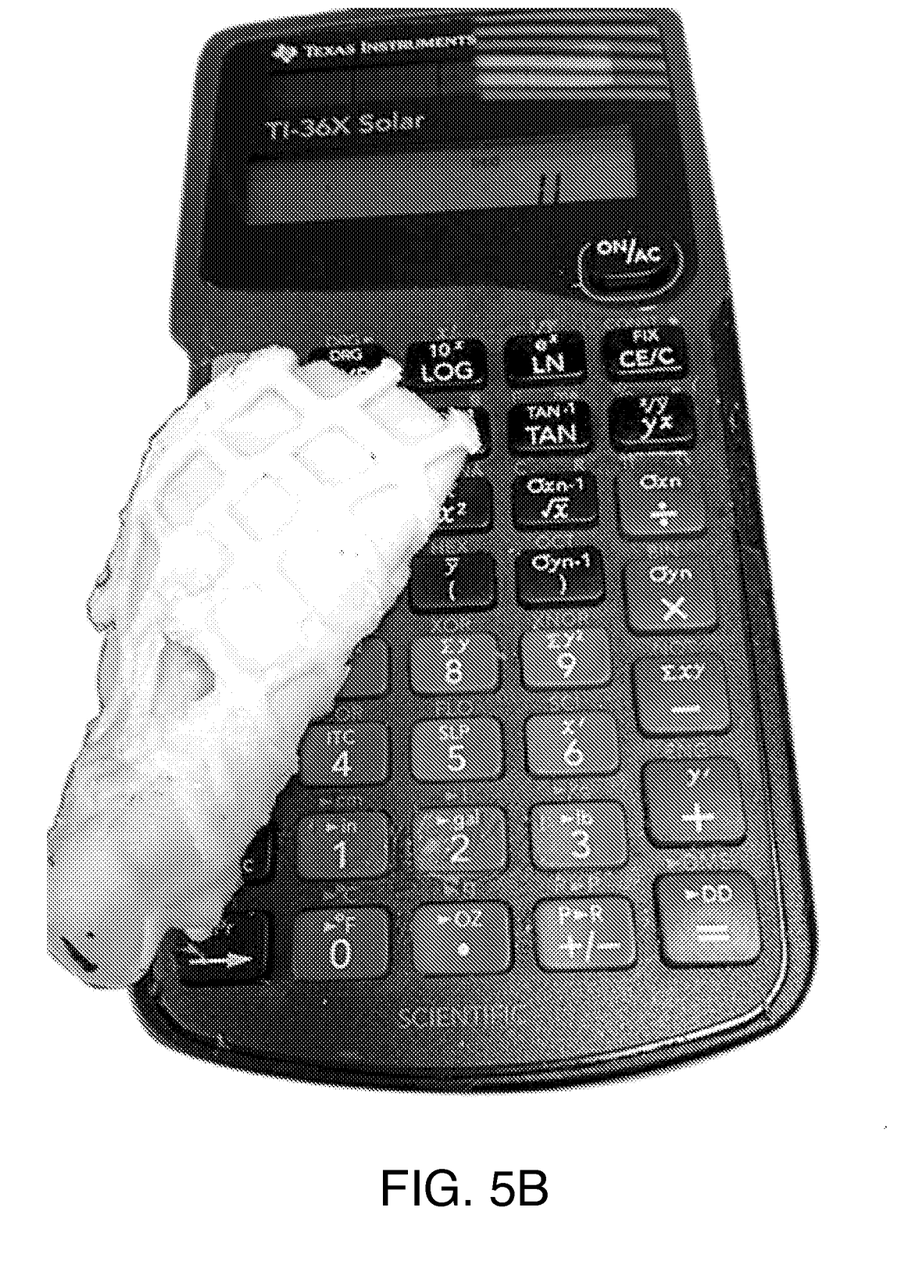

Referring now to FIGS. 5A to 5B, shown are photographs demonstrating how the antimicrobial cleaning composition of the present disclosure can be used to clean and disinfect an instrument keyboard in one step. An effective amount of the antimicrobial cleaning composition (30 g of FAB, 60 g of GenFlo® 3000 [20% wt/wt solids in water and emulsified styrene-butadiene copolymer, Omnova Solutions Inc., Mogadone, Ohio], 5% wt/wt benzalkonium chloride and 3% wt/wt hydrogen peroxide), was poured onto the instrument keyboard (Texas Instruments TI-36X Solar model calculator), see FIG. 5A. The antimicrobial cleaning composition was allowed to cure for 40 minutes. The cured composition was peeled off as a drapeable film. The viscosity of the antimicrobial cleaning composition was high enough to prevent it from seeping into the inner portion of the calculator and potentially shorting the calculator's electronic components. See FIG. 5B showing how the composition coated and covered the keys without going under the keys and into the body of the calculator. The coating covered the keys and the surrounding base plate to clean and disinfect the entire keyboard.

Experimental Data

Zone of Inhibition Testing:

Zone of inhibition testing with a variety of gram negative and gram positive bacteria was performed. The test material was brought into contact with a known amount of test microorganisms on an agar plate for 48 hours at ambient temperature. At the end of the contact time the diameter of inhibited colony formation (zone of inhibition) surrounding the test material was measured. Table 2 below shows the results of the zone of inhibition testing. Larger values for zone of inhibition indicate more active is released. The results suggest that the antimicrobial cleaning agent acts as a controlled release matrix, allowing the antimicrobial agent (s) to yield a significant zone of inhibition.

TABLE 2

| Codes | P. aeroginosa ZOI* (cm) | E. coli ZOI* (cm) | S. aureus ZOI* (cm) |
|---|---|---|---|
| 5% wt/wt Quat in SP | 0.0 | 3.0 | 4.4 |
| 1.25% wt/wt Quat in SP | 0.0 | 3.5 | 4.7 |
| 3% wt/wt H$_2$O$_2$ in SP | 0.0 | 3.9 | 5.3 |
| 5% Quat with 3% H$_2$O$_2$ in FAB | 3.9 | 5.9 | 7.0 |
| Negative Control | | 0.0 | |
| Positive Control (n = 1) | | 1.9 | |
| Desiccation Control** (n = 2) | | 0.0 | |

"FAB" = superabsorbent polymer material of the present disclosure
"Quat" = benzalkonium chloride (USP Mason Chemical, Arlington Heights, IL)
"H$_2$O$_2$" = hydrogen peroxide (Sigma-Aldrich Chemical Co., Milwaukee, WI)
"Negative Control" = FAB film with no additives
"Positive Control" = 5 µg disk of vancomycin Tensile Testing:

Referring to Table 3, the following inorganic particles were added to the antimicrobial cleaning composition and cured. The Arizona sand (available from CR Minerals Co., Golden, Colo., U.S.A.) and pumice (available from Charles B. Crystal Co., New York, N.Y., U.S.A.) demonstrated effective integrity and strength. The surface of these porous absorbent structures was similar to a fine-grit sandpaper. The bentonite particles (available from Acros Organics, Fair Lawn N.J., U.S.A) formed a material with relatively high peak load values. The diatomaceous earth (available from Aldrich Chemical Company, Milwaukee Wis., U.S.A.) and silica samples (Sigma-Aldrich Chemical Co. Milwaukee Wis., U.S.A.) formed structures that were not able to be tested due to their lack of integrity. One possible reason for this is that these particles provided too much cross-linking capability within the example.

TABLE 3

| Sample Description | Sample Thickness (mm) | Peak Load (gF) | Peak Stretch (%) | Peak Energy (g/cm) | Particle Size (µm) |
|---|---|---|---|---|---|
| Arizona sand | 1.14 | 2023.1 | 7.3 | 740.6 | 30 |
| Bentonite | 1.46 | >100N | not tested | not tested | 75 |
| Chalk | 1.62 | 1028.3 | 80.5 | 1722.9 | 30 |
| Diatomaceous earth | 1.46 | Brittle | n/a | n/a | 3 |
| Pumice | 1.76 | >100N | 37.1 | 957.3 | 35 |
| Silica | 1.81 | brittle | n/a | n/a | 300-600 |
| Silica (nanoparticle) | 1.50 | brittle | n/a | n/a | 0.014 |

Based on the above samples, desirable embodiments of the antimicrobial cleaning composition mixed with inorganic particles may have a Peak Energy of at least about 150 g/cm, or in another aspect, at least about 500 g/cm.

Test Methods

Figure 6:
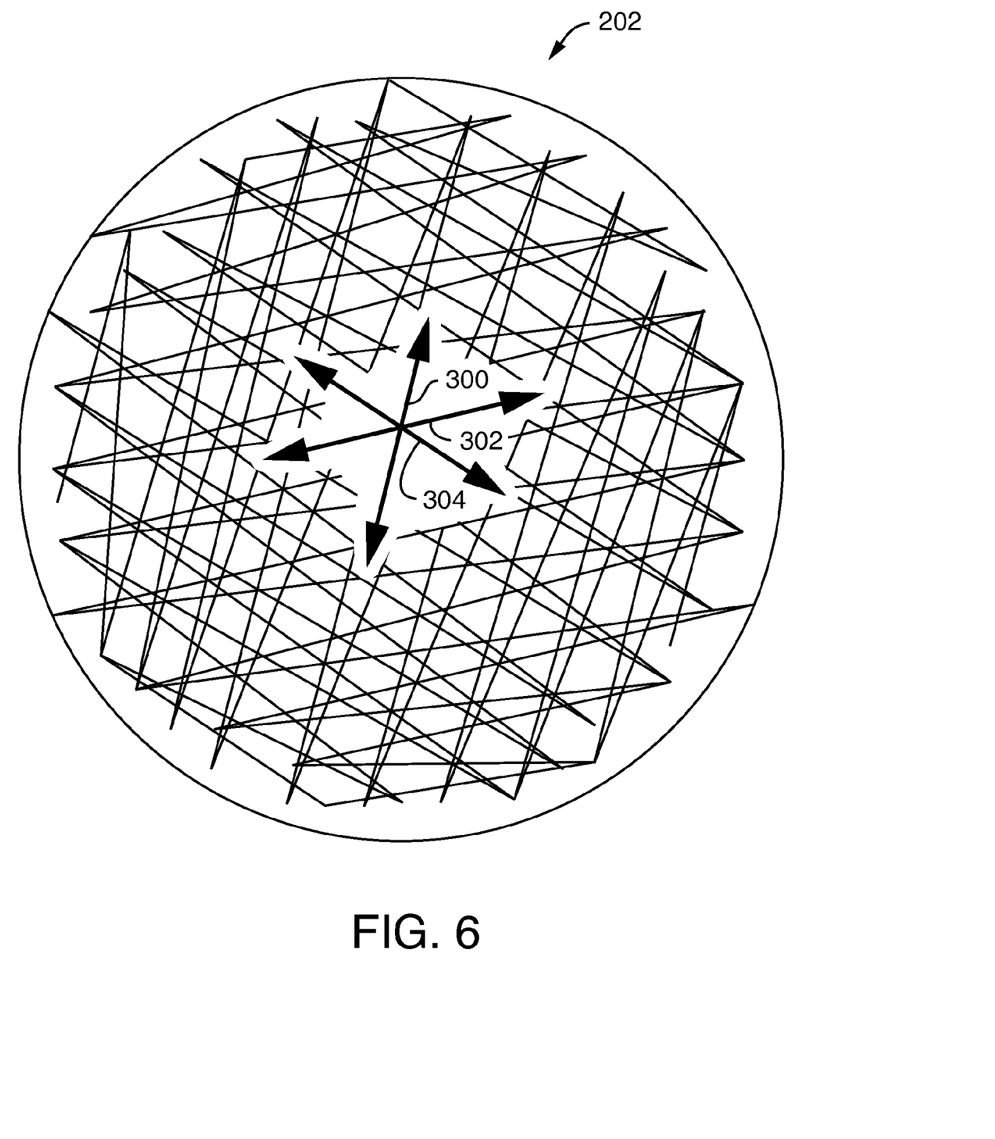
FIG. 6 is a plan view of an agar plate and the directions in which it is inoculated for the Zone of Inhibition Test.

Zone of Inhibition Test:

Referenced method AATCC 147-1998 "Antibacterial Activity Assessment of Textile Materials: Parallel Streak Method" with changes for following Zone of Inhibition procedure (AATCC is "American Association of Textile Chemists and Colorists" located in Research Triangle Park, N.C.):

Organisms used in this study were *Escherichia coli* (ATCC 11229)/*Staphylococcus aureus* (ATCC 6538)/*Pseudomonas aeruginosa* (ATCC 27853) (ATCC is "American Type Culture Collection" an organization in Manassas, Va.). Washed cells were diluted in Butterfield's Phosphate buffer to a target titer of approximately $10^8$ colony forming units (CFU)/mL. Agar plates for testing were brought to room temperature prior to inoculation. A sterile applicator swab was placed in cell suspension and excess fluid was expressed using the side of the centrifuge tube. Referring to FIG. 6, the entire surface of each agar plate 202 was inoculated by covering the surface completely in three different directions 300, 302, 304 to ensure uniform growth. Inoculated plates were stored at ambient temperature for 10-15 minutes prior to application of test samples, one sample per plate. The test material was cut into 1.5 by 1.5 cm squares and applied to the center of each inoculated plate. Plates were stored upright at ambient temperature for 48 hours. At the end of the contact time, the diameter of inhibited colony formation (zone of inhibition) surrounding the test material was measured.

Tensile Test:

The tensile testing was performed as follows.

a. Equipment. MTS Insight Electromechanical 1 kN Extended Length; 100N load cell (Model 820-1XLTEL/0060) (MTS Systems Corp., Eden Prairie, Minn.); rubber coated grips.

b. Crosshead speed. 305+/−10 mm/minute c. Specimen preparation. The Specimens were free of folds, wrinkles or any distortions. Specimens were cut from a sample such that they were evenly spaced across the directional width of same. The cut specimens were 6 cm square. (There is no machine- or cross-direction because the material is isotropic.) The thickness of each sample was measured using a digital caliper.

c. Test environment. 23 C+/−2 C; 50%+/−5% relative humidity. Specimens were conditioned in the test environment for at least 24 hours. Vinyl gloves were used to handle specimens.

d. Reports. Test values reported in Table 2 include Peak Load, Peak Stretch and Peak Energy. Peak Stretch is a measure of the ductility of a material. It is the increase in the length of the sample measured after failure (that is, the length of the sample after failure minus the original sample length) divided by original sample length. Higher elongation indicates higher ductility. Peak Energy is the energy absorbed by the sample up to the point of maximum load. For the samples reported in Table 2, the maximum load corresponded to either failure (the energy the sample can absorb before failing) or an amount greater than 100N. Peak Load, as reported in the tables, is the highest value reached by the sample during a test.

Residual Monoethylenically Unsaturated Monomer Test:

The residual monoethylenically unsaturated monomer analysis is carried out using solid film obtained from the polymer solution or superabsorbent composition. By way of example for this test description, the monoethylenically unsaturated monomer was acrylic acid. High performance liquid chromatography (HPLC) with a SPD-10Avp Shimadzu UV detector (available from Shimadzu Scientific Instruments, having a place of business in Columbia, Md., U.S.A) was used to determine the residual acrylic acid monomer content. To determine the residual acrylic acid monomer, about 0.5 grams of cured film was stirred in 100 ml of a 0.9% NaCl-solution for 16 h using a 3.5 cm L×0.5 cm W magnetic stirrer bar at 500 rpm speed. The mixture was filtered and the filtrate passed through a Nucleosil C8 100A reverse phase column (available from Column Engineering Incorporated, a business having offices located in Ontario, Calif., U.S.A.) to separate the acrylic acid monomer. The acrylic acid monomer elutes at a certain time with detection limit at about 10 ppm. The peak area of resulting elutes, calculated from the chromatogram, was then used to calculate the amount of residual acrylic acid monomer in the film. Initially, a calibration curve was generated by plotting the response area of pure acrylic acid elutes against its known amount (ppm). A linear curve with a correlation coefficient of greater than 0.996 was obtained.

16 Hr Extractable Test (%)

The following test methods are used to calculate the 16-hour extractable levels for the superabsorbent composition. The first test method is intended for use on carboxylic acid based superabsorbent materials. About 0.5 g of cure film obtained from the polymer solution is placed into a 250 ml conical flask containing 100 ml 0.9% NaCl solution. The mixture was stirred with a 3.5 cm L×0.5 cm W magnetic stirrer bar at 500 rpm speed for 16 hours. The sample was then filtered using WHATMAN #3 filter paper (available from Whatman, Inc., a business having offices located in Florham Park, N.J., U.S.A.) and an aspirator attached to a water faucet created a vacuum in the filtration unit by sucking air with running water. The entire solution was filtered and special care was taken to ensure that no fluid was lost and that no solid material passed through or around the filter paper. About 50 g the filtered solution was then taken into a 100 ml beaker. The pH of the solution was adjusted to 8.5 stepwise by using 1.0N NaOH and 0.1N HCl. The resulting solution was titrated to pH 3.9 using the Brinkman Titoprocessor (available from Brinkmann Instruments, Inc., a business having offices located in Westbury, N.Y., U.S.A.). The results were calculated by weight basis, with an assumed sodium/hydrogen acrylate formula weight of 87.47. The formula weight was derived from that of 70% neutralized acrylic acid.

Centrifuge Retention Capacity (CRC) Test:

As used herein, the Centrifugal Retention Capacity (CRC) is a measure of the Absorbent Capacity of the superabsorbent polymer composition retained after being subjected to centrifugation under controlled conditions. The CRC can be measured by placing a sample of the material to be tested into a water-permeable bag that will contain the sample while allowing the test solution (0.9 percent NaCl solution) to be freely absorbed by the sample. A heat-sealable tea bag material (available from Dexter Nonwovens of Windsor Locks, Conn., U.S.A., as item #11697) works well for most applications. The bag was formed by folding a 5-inch by 3-inch sample of the bag material in half and heat sealing two of the open edges to form a 2.5-inch by 3-inch rectangular pouch. The heat seals were about 0.25 inch inside the edge of the material. After the sample was placed in the pouch, the remaining open edge of the pouch was also heat-sealed. Empty bags were also made to be tested with the sample bags as controls. The sample dimension was chosen such that the teabag did not restrict the swelling of the material, generally with dimensions smaller than the sealed bag area (about 2-inch by 2.5-inch). Three sample bags were tested for each material.

The sealed bags were submerged in a pan of 0.9 percent NaCl solution. After wetting, the samples remained in the solution for 60 minutes, at which time they were removed from the solution and temporarily laid on a non-absorbent flat surface.

The wet bags were then placed into the basket of a suitable centrifuge capable of subjecting the samples to a g-force of 350. (A suitable centrifuge is a Heraeus LABOFUGE 400, Heraeus Instruments, part number 75008157, available from Heraeus Infosystems GmbH, Hanau, Germany). The bags were centrifuged at a target of 1600 rpm, but within the range of 1500-1900 rpm, for 3 minutes (target g-force of 350). The bags were removed and weighed. The amount of fluid absorbed and retained by the material, taking into account the fluid retained by the bag material alone, is the Centrifugal Retention Capacity of the material, expressed as grams of fluid per gram of material.

Viscosity after 16 Hours Test:

Viscosity of the flexible binder polymer solution was measured using a Brookfield DVII+ Programmable viscometer (available from Brookfield Engineering, a business having offices located at Middleboro, Mass., U.S.A.). About 200-250 ml of binder composition is taken in a 25-ounce plastic cup. The viscometer was zeroed initially with a desired Spindle. For binder composition, Spindle Number 3 was used. The viscosity was measured at 20 RPM and at temperature 22±1° C.

Percent Solids Test:

About 20±0.5 g of flexible superabsorbent binder polymer composition was weighed (W1) into a tared (W2) hexagonal plastic weighing dish. The approximate internal diameter (ID) of weighing dish was 5 inch/3.5 inch (Top/Base). The polymer composition-containing dish was placed in a fuming hood at room temperature for about 16-20 hours. The dish containing partially dried solid film was then placed into a laboratory oven pre-heated at 80° C. for 30 minutes. The dish and its content were allowed to cool to room temperature. The dried dish with resulting solid film was then weighed together (W3). The percent solids is calculated using the following formula:

% Solids=[(W3−W2)/(W1−W2)]×100

The present disclosure has been described in general and in detail by means of examples. Persons of skill in the art understand that the disclosure is not limited necessarily to the embodiments specifically disclosed, but that modifications and variations may be made without departing from the scope of the disclosure as defined by the following claims or their equivalents, including other equivalent components presently known, or to be developed, which may be used within the scope of the present disclosure. Therefore, unless changes otherwise depart from the scope of the disclosure, the changes should be construed as being included herein.

What is claimed is:

1. A method of disinfecting a hard surface comprising the steps of:
providing an antimicrobial cleaning composition comprised of a liquid flexible superabsorbent polymer material, and an antibacterial agent having a disinfection period;
applying the antimicrobial cleaning composition onto the hard surface to be disinfected;
allowing the antimicrobial cleaning composition to cure no faster than the disinfection period; and
removing the dried antimicrobial cleaning composition from the hard surface by peeling away the dried antimicrobial cleaning composition as a continuous drapeable film.

2. The method of claim 1 wherein the flexible superabsorbent polymer material has less than about 1000 parts per million residual monoethylenically unsaturated monomer.

3. The method of claim 1 wherein the monoethylenically unsaturated monomer is acrylic acid.

4. The method of claim 1 further comprising the step of adding texturizing particles, wherein the ratio by weight of superabsorbent polymer material to particles in the composition is less than 6:1.

5. The method of claim 1 wherein the antimicrobial cleaning composition has a viscosity of less than 10,000 cps.

6. The method of claim 1 wherein the antimicrobial cleaning composition has a viscosity of 50,000 cps or greater.

7. The method of claim 4 wherein the texturizing particles have an average ratio of length to width of less than 5.

8. A method of removing a contaminant from a hard surface and disinfecting same, the method comprising the steps of:
providing an antimicrobial cleaning composition comprising
an antimicrobial agent, wherein the antimicrobial agent is selected from the group consisting of a quaternary ammonium compound, a peroxide, a surfactant, silver, copper, a biguanide, an isothiazolinone, an alcohol, an acid, a hypochlorite, iodine, a phenolic, potassium monopersulfate, chlorine dioxide, an anilide, a pyrithione, an antimicrobial peptide, and combinations thereof;
a liquid superabsorbent polymer comprising acrylic acid; and
an active agent selected from the group consisting of calcium chloride, glycerol, a surfactant, and combinations thereof;
applying the antimicrobial cleaning composition onto the hard surface so that it covers the contaminant;
drying the antimicrobial cleaning composition to induce cross-linking in the superabsorbent polymer material to transition the liquid composition into a solid state, and allowing the antimicrobial cleaning composition to bond to the contaminant; and
removing the dried antimicrobial cleaning composition and bonded contaminant from the hard surface after the antimicrobial agent has effectively disinfected same by peeling away the dried antimicrobial cleaning composition and bonded contaminant from the hard surface as a continuous drapeable film.

9. The method of claim 8 wherein the contaminant comprises a liquid material.

10. The method of claim 8 wherein the contaminant comprises a solid material.

11. The method of claim 8 wherein the step of applying the antimicrobial cleaning composition onto the hard surface is performed by spraying.

12. The method of claim 8 wherein the step of applying the antimicrobial cleaning composition onto the hard surface is performed by rolling.

13. The method of claim 11 wherein the antimicrobial cleaning composition is applied to the hard surface as a foam.

14. A method of cleaning a contaminant from a hard surface comprising the steps of:
covering the contaminants with a liquid superabsorbent polymer comprising acrylic acid;
drying the liquid superabsorbent polymer so that it bonds to the contaminants; and removing the liquid superabsorbent polymer and contaminants from the hard surface by peeling away the dried superabsorbent polymer and contaminants from the hard surface as a continuous drapeable film.

15. The method of claim 14 wherein the hard surface comprises a keyboard.

16. The method of claim 14 wherein the contaminant is in solid form.

17. The method of claim 14 wherein the contaminant is body matter selected from the group consisting of oils, blood, urine, gastric juice, fecal matter, saline, vomit, human tissue, and mucus.

18. The method of claim 14 wherein the contaminant is selected from the group of glass, food stuff, and dust.

\* \* \* \* \*